United States Patent
Campin et al.

(10) Patent No.: US 6,569,154 B2
(45) Date of Patent: May 27, 2003

(54) OPTIMIZATION OF ABLATION CORRECTION OF AN OPTICAL SYSTEM AND ASSOCIATED METHODS

(75) Inventors: John Alfred Campin, Orlando, FL (US); George H. Pettit, Maitland, FL (US)

(73) Assignee: Alcon, Inc., Hunenberg (CH)

( * ) Notice: Subject to any disclaimer, the term of this patent is extended or adjusted under 35 U.S.C. 154(b) by 98 days.

(21) Appl. No.: 09/814,398

(22) Filed: Mar. 22, 2001

(65) Prior Publication Data

US 2002/0007176 A1 Jan. 17, 2002

Related U.S. Application Data

(60) Provisional application No. 60/191,187, filed on Mar. 22, 2000.

(51) Int. Cl.$^7$ ............................................... A61B 17/00
(52) U.S. Cl. .............................. 606/5; 606/10; 606/12; 356/300; 356/601; 351/212; 128/898
(58) Field of Search ........................... 606/4–6, 10–12; 356/300, 319–322, 314, 603–608, 601; 351/204, 211–215; 128/898

(56) References Cited

U.S. PATENT DOCUMENTS

| | | | |
|---|---|---|---|
| 4,420,228 A | * 12/1983 | Humphrey | 351/212 |
| 4,669,466 A | 6/1987 | L'Esperance | |
| 4,688,941 A | 8/1987 | Philbert | |
| 4,750,818 A | 6/1988 | Cochran | |
| 5,106,183 A | 4/1992 | Yoder, Jr. | |
| 5,221,834 A | 6/1993 | Lisson et al. | |
| 5,233,174 A | 8/1993 | Zmek | |
| 5,339,121 A | 8/1994 | Shimmick et al. | |
| 5,452,031 A | 9/1995 | Ducharme | |
| 5,493,391 A | 2/1996 | Neal et al. | |
| 5,632,742 A | * 5/1997 | Frey et al. | 606/12 |
| 5,684,545 A | 11/1997 | Dou et al. | |
| 5,777,719 A | 7/1998 | Williams et al. | |
| 5,822,035 A | 10/1998 | Bille | |
| 5,841,511 A | 11/1998 | D'Souza et al. | |
| 5,849,006 A | * 12/1998 | Frey et al. | 606/5 |
| 5,949,521 A | 9/1999 | Williams et al. | |
| 6,271,915 B1 | * 8/2001 | Frey et al. | 356/124 |
| 6,280,435 B1 | * 8/2001 | Odrich et al. | 606/5 |
| 6,322,216 B1 | * 11/2001 | Yee et al. | 351/210 |
| 6,413,251 B1 | * 7/2002 | Williams | 606/5 |
| 6,460,997 B1 | * 10/2002 | Frey et al. | 351/211 |

OTHER PUBLICATIONS

Liang, et al., "Objective Measurement of Wave Aberrations of the Human Eye with the Use of a Hartmann–Shack Wave–front Sensor," *J. Opt. Soc. Am. A*, vol. 11, No. 7, Jul. 1994, pp. 1949–1957.

(List continued on next page.)

*Primary Examiner*—Linda C. M. Dvorak
*Assistant Examiner*—Ahmed M. Farah
(74) *Attorney, Agent, or Firm*—Allen, Dyer, Doppelt, Milbrath & Gilchrist, P.A.

(57) ABSTRACT

An optical correction system for correcting visual defects of an eye includes a wavefront analyzer responsive to a wavefront emanating from an eye for determining an optical path difference between a reference wave and the wavefront. A converter provides an optical correction based on the path difference and on a radially dependent ablation efficiency. The efficiency correction uses a compensating polynomial of the form $A+B\rho+C\rho^2+D\rho^3+\ldots+X\rho^n$, where $\rho$ is a normalized radius measured from a central portion of the cornea, reaching a value of 1 at an outer edge of the optical correction zone. A laser beam is directed to the cornea that has power sufficient for ablating corneal material. The optical correction is achieved by the removal of a selected amount of the corneal material to create a desired corneal shape change based on the optical correction.

33 Claims, 5 Drawing Sheets

OTHER PUBLICATIONS

Roberts, "Characterization of the Inherent Error in a Spherically–Biased Corneal Topography System in Mapping a Radially Aspheric Surface," *Journal of Refractive & Corneal Surgery*, vol. 10, Mar./Apr. 1994, pp. 103–111.

Charman, "Wavefront Aberration of the Eye: A Review," *Optometry and Vision Science*, vol. 68, No. 8, pp. 574–583.

Gauthier, et al., "Factors Affecting Epithelial Hyperplasia After Photorefractive Keratectomy," *J Cataract Refract Surgery*, vol. 23, Sep. 1991, pp. 1042–1050.

Förster, MD, et al., "Steep Central Islands After Myopic Photorefractive Keratectomy," *J Cataract Refract Surgery*, vol. 24, Jul. 1998, pp. 899–904.

Munnerlyn, Ph.D., et al., "Photorefractive Keratectomy: A Technique for Laser Refractive Surgery" *J Cataract Refract Surgery*, vol. 14, Jan. 1988, pp. 46–52.

Wilson, "Structure of the Corneal Stroma," *Vision Res.*, vol. 10, Oct. 1969, pp. 519–520.

Vinciguerra, et al., "Photorefractive Keratoplasty I," Investigative Ophthalmology & Visiual Science, vol. 36, No. 4, pp. 81.

* cited by examiner

OPTIMIZATION OF ABLATION CORRECTION OF AN OPTICAL SYSTEM AND ASSOCIATED METHODS

CROSS-REFERENCE TO RELATED APPLICATION

This application claims priority to provisional application Ser. No. 60/191,187, filed Mar. 22, 2000, "Optimizing Refractive Surgery Ablation Profiles by Compensating for Ablation Effectiveness Function."

BACKGROUND OF THE INVENTION

1. Field of the Invention

The present invention relates to optical aberration measurement and correction, and, more particularly, to a system and method for achieving an empirical optimization of an objective measurement and correction of an optical system such as the human eye.

2. Description of Related Art

Optical systems having a real image focus can receive collimated light and focus it at a point. Such optical systems can be found in nature, e.g., human and animal eyes, or can be manmade, e.g., laboratory systems, guidance systems, and the like. In either case, aberrations in the optical system can affect the system's performance.

A perfect or ideal human eye diffusely reflects an impinging light beam from its retina through optics of the eye, which includes a lens and a cornea. For such an ideal eye in a relaxed state, i.e., not accommodating to provide near-field focus, reflected light exits the eye as a sequence of plane waves. However, a real eye typically has aberrations that cause deformation or distortion of reflected light waves exiting the eye. An aberrated eye diffusely reflects an impinging light beam from its retina through its lens and cornea as a sequence of distorted wavefronts.

It is known in the art to perform laser correction of focusing deficiencies by photorefractive keratectomy (PRK), which modifies corneal curvature, and LASIK surgery. Such methods typically employ a 193-nm excimer laser to ablate corneal tissue. Munnerlyn et al. (*J. Cataract Refract Surg.* 14(1), 46–52, 1988) have presented equations for determining a specific volume of tissue to be removed to achieve a desired refractive correction. Frey (U.S. Pat. No. 5,849,006) teaches a method of using a small-spot laser to remove a desired volume of tissue for effecting a desired refractive correction.

SUMMARY OF THE INVENTION

It is an object of the present invention to provide a system and method for optimizing an ablative correction to a human cornea.

It is a further object to provide such a system and method that accounts for corneal anisotropy.

It is another object to provide such a system and method that includes a radially dependent attenuation of the ablation power.

It is an additional object to provide such a system and method utilizing a mathematical description that can readily be adapted into an ablation algorithm.

These and other objects are achieved by the present invention, an optical correction system for correcting visual defects of an eye. The system comprises a wavefront analyzer responsive to a wavefront emanating from an eye for determining an optical path difference between a reference wave and the wavefront. The system further comprises a converter for providing an optical correction based on the path difference and on a radially dependent ablation efficiency. The efficiency correction uses a compensating polynomial of the form $A+B\rho+C\rho^2+D\rho^3+\ldots+X\rho^n$, where $\rho$ is a normalized radius that is optical zone specific and is measured from a central portion of the cornea, reaching a value of 1 at the edge of the optical correction zone.

A laser beam is directed to the cornea that has power sufficient for ablating corneal material. The optical correction is achieved by the removal of a selected amount of the corneal material to create a desired corneal shape change based on the optical correction.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 4A plots $1-0.3r^2$, where $r_{max}=3.25$ mm; FIG. 4B plots $0.95-0.3r^2-0.25r^3+0.3r^4$.

DETAILED DESCRIPTION OF THE PREFERRED EMBODIMENTS

Figure 1:
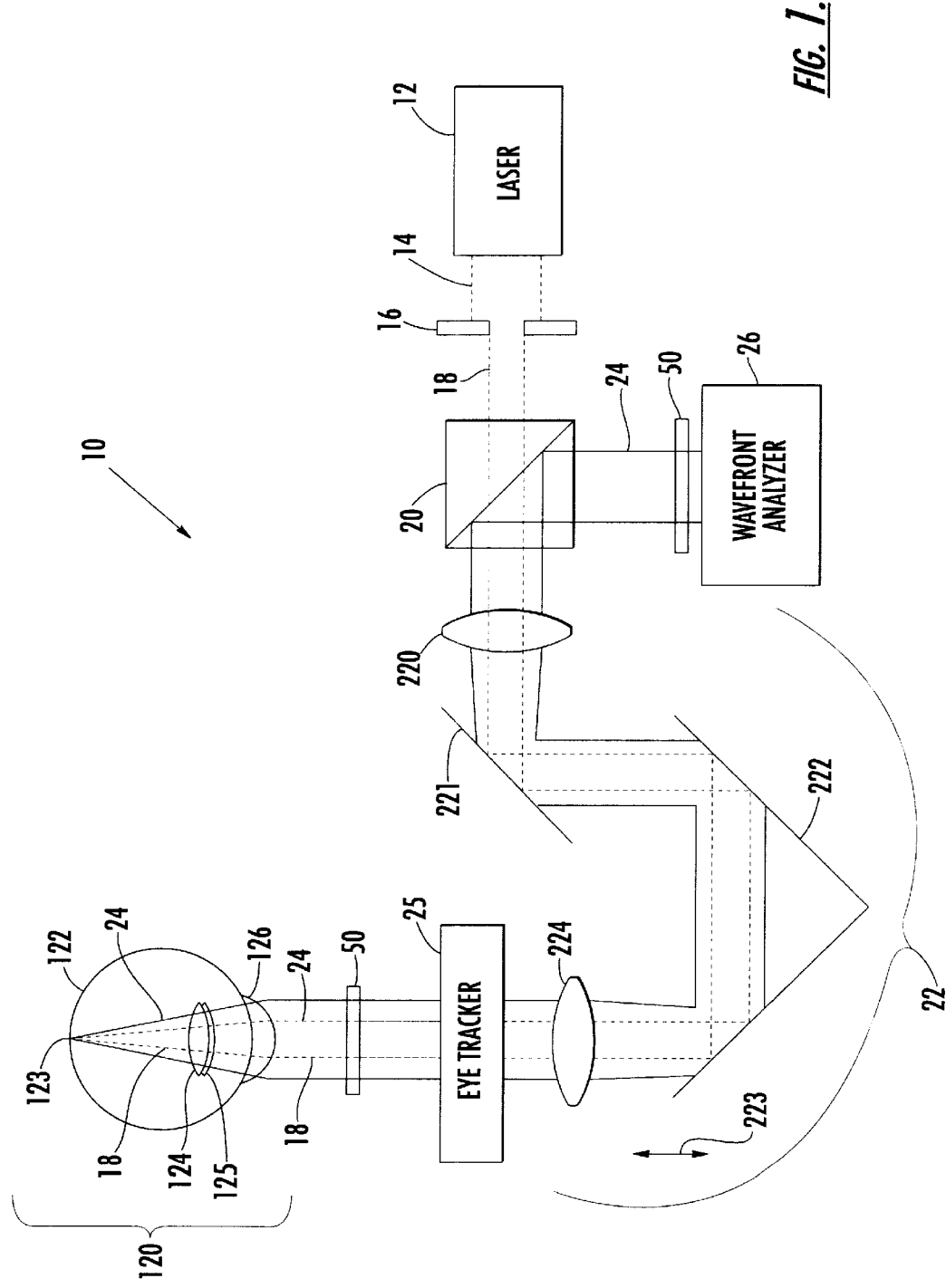
FIG. 1 is a schematic diagram of a system for determining ocular aberrations.
Figure 2:
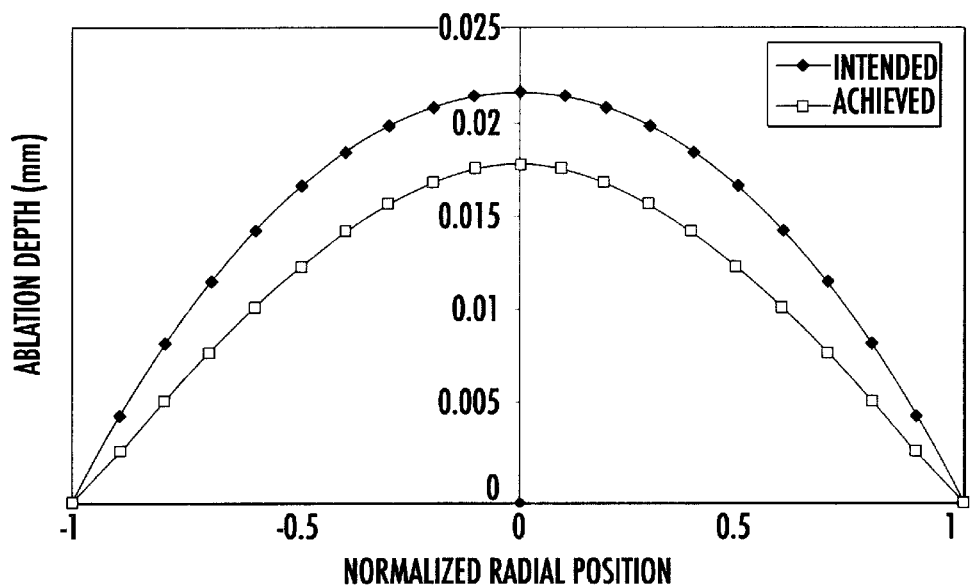
FIG. 2 is a graph of desired and achieved ablation depths as a function of radial position for a myopic eye.
Figure 3:
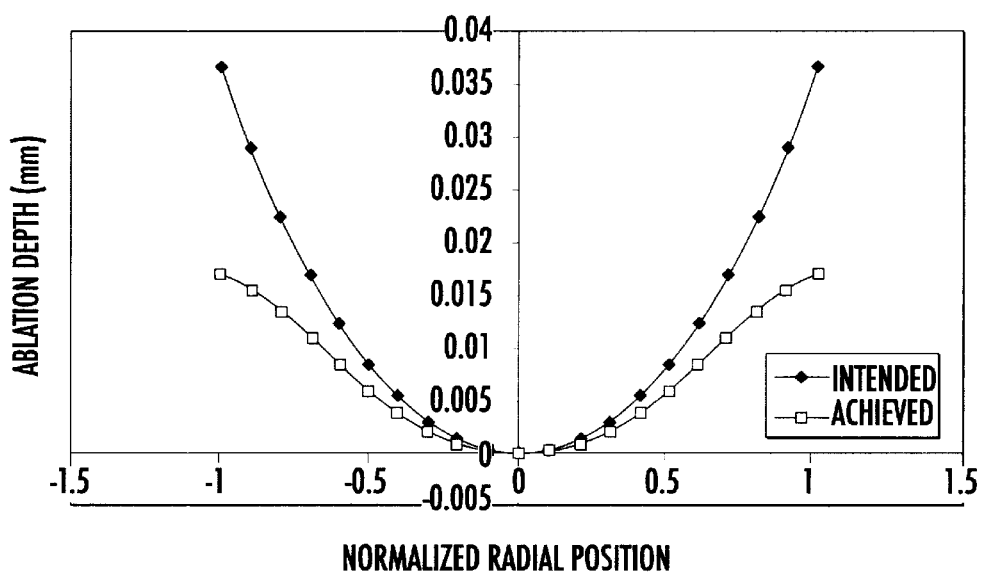
FIG. 3 is a graph of desired and achieved ablation depths as a function of radial position for a hyperopic eye.

A description of the preferred embodiments of the present invention will now be presented with reference to FIGS. 1–5.

The system and method for correcting visual defects of an eye includes a wavefront analyzer, in a preferred embodiment a system 10 (FIG. 1) similar to that described in copending and co-owned application Ser. No. 09/664,128, the contents of which are incorporated herein by reference. The apparatus 10 includes a laser 12 for generating optical radiation used to produce a small-diameter laser beam 14. The laser 12 generates a collimated laser light beam (represented by dashed lines for the beam 14) of a wavelength and power that is eye-safe. For ophthalmic applications, appropriate wavelengths would include the entire visible spectrum and the near-infrared spectrum. By way of example, appropriate wavelengths may be in a range of from approximately 400–1000 nms, including 550-, 650-, and 850-nm useful wavelengths. While operation in the visible spectrum is generally desired, since these are the conditions in which the eye operates, the near-infrared spectrum may offer advantages in certain applications. For example, the patient's eye may be more relaxed if the patient does not know measurement is taking place. Regardless of the wavelength of the optical radiation, power should be restricted in ophthalmic applications to eye-safe levels. For laser radiation, appropriate eye-safe exposure levels can be found in the U.S. Federal Performance Standard for Laser Products. If the analysis is to be performed on an optical system other than the eye, the examination wavelength range logically should incorporate the intended performance range of the system.

To select a small-diameter collimated core of laser light beam 14, an iris diaphragm 16 is used to block all of laser light beam 14 except for the laser beam 18 of a size desired for use. In terms of the present invention, the laser beam 18 will have a diameter in the range of approximately 0.5–4.5 mm, with 1–3 mm being typical, by way of example. A badly aberrated eye uses a smaller-diameter beam, while an eye with only slight aberrations can be evaluated with a larger-diameter beam. Depending on the output divergence of the laser 12, a lens can be positioned in the beam path to optimize collimating of the beam.

Laser beam 18, as herein described by way of example, is a polarized beam that is passed through a polarization-sensitive beam splitter 20 for routing to a focusing optical train 22, which operates to focus the laser beam 18 through the optics of the eye 120 (e.g., the cornea 126, pupil 125, and the lens 124) to the retina 122. It is to be understood that the lens 124 may not be present for a patient that has undergone a cataract procedure. However, this does not affect the present invention.

The optical train 22 images the laser beam 18 as a small spot of light at or near the eye's fovea centralis 123, where the eye's vision is most acute. Note that the small spot of light could be reflected off another portion of retina 122 in order to determine aberrations related to another aspect of one's vision. For example, if the spot of light were reflected off the area of the retina 122 surrounding the fovea centralis 123, aberrations specifically related to one's peripheral vision could then be evaluated. In all cases, the spot of light may be sized to form a near-diffraction-limited image on the retina 122. Thus the spot of light produced by laser beam 18 at fovea centralis 123 does not exceed approximately 100 $\mu$m in diameter and, typically, is on the order of 10 $\mu$m.

The diffuse reflection of the laser beam 18 back from the retina 122 is represented by solid lines 24 indicative of radiation that passes back through the eye 120. The wavefront 24 impinges on and is passed through the optical train 22 and on to the polarization-sensitive beam splitter 20. The wavefront 24 is depolarized relative to the laser beam 18 due to reflection and refraction as the wavefront 24 emanates from the retina 122. Accordingly, the wavefront 24 is turned at the polarization-sensitive beam splitter 20 and directed to a wavefront analyzer 26 such as a Hartmann-Shack (H-S) wavefront analyzer. In general, the wavefront analyzer 26 measures the slopes of wavefront 24, i.e., the partial derivatives with respect to x and y, at a number of (x, y) transverse coordinates. This partial derivative information is then used to reconstruct or approximate the original wavefront with a mathematical expression such as a weighted series of Zernike polynomials.

The polarization states for the incident laser beam 18 and the beam splitter 20 minimizes the amount of stray laser radiation reaching the sensor portion of the wavefront analyzer 26. In some situations, stray radiation may be sufficiently small when compared to the radiation returning from the desired target (e.g., the retina 122) so that the polarization specifications are unnecessary.

The present invention is able to adapt to a wide range of vision defects and as such achieves a new level of dynamic range in terms of measuring ocular aberrations. Dynamic range enhancement is accomplished with the optical train 22 and/or a wavefront sensor portion of the wavefront analyzer 26. The optical train 22 includes a first lens 220, a flat mirror 221, a Porro mirror 222, and a second lens 224, all of which lie along the path of laser beam 18 and the wavefront 24. The first lens 220 and the second lens 224 are identical lenses maintained in fixed positions. The Porro mirror 222 is capable of linear movement, as indicated by arrow 223 to change the optical path length between the lenses 220 and 224. However, it is to be understood that the present invention is not limited to the particular arrangement of the flat mirror 221 and the Porro mirror 222 and that other optical arrangements may be used without departing from the teachings and benefits of the present invention.

A "zero position" of the Porro mirror 222 is identified by replacing the eye 120 by a calibration source of collimated light to provide a reference wavefront such as a perfect plane wave 110. Such a source could be realized by a laser beam expanded by a beam telescope to the diameter that will cover the imaging plane of wavefront analyzer 26 and adjustment of the Porro mirror 222 until the wavefront analyzer 26 detects the light as being collimated. Note that the changes in optical path length brought about by the Porro mirror 222 can be calibrated in diopters to provide an approximate spherical dioptric correction.

In order to empirically determine a treatment efficiency of a particular beam profile in effecting a desired change in refraction, data were collected on the ablation of human corneas in vivo with known ablation profiles and known laser beam fluence profiles. The precision and lack of subjectivity of the above-discussed wavefront measurement was used to determine the optical results and hence the effective treatment efficiency of particular ablation profiles. Any deviations from the expected change in aberration content can be attributed to relative differences in ablation effectiveness across the corneal surface.

A single generalized ablation effectiveness function was derived from clinical data using both myopic and hyperopic nominal ablation profiles. The data were collected from nominal ablation profiles obtained using an excimer laser narrow-beam scanning spot such as that disclosed in U.S. Pat. Nos. 5,849,006 and 5,632,742, the contents of which are incorporated by reference herein.

The radially symmetric attenuation function of the present invention was determined by analysis of graphs of intended and achieved ablation depth versus normalized radial corneal position for myopic (FIG. 2) and hyperopic (FIG. 3) eyes. In its general form the ablation effectiveness function has the polynomial form $A+B\rho+C\rho^2+D\rho^3+ \ldots +X\rho^n$, as described above. In a specific embodiment the function has the form $A+B\rho+C\rho^2+D\rho^3+E\rho^4$, with exemplary coefficients $A\cong 0.95$, $B\cong 0$, $C\cong -0.3$, $D=-0.25$, and $E=0.3$ for an optical zone radius of 3.25 mm. The ablation effectiveness function includes any radial dependence in the actual ablation rate, that is, for example, micrometers of tissue removed per pulse. However, it also incorporates any biomechanical effect or intrinsic variation in corneal optical properties that can influence the optical outcome in a radially dependent manner.

The attenuation or efficiency function is then used to modify the treatment profile by taking the desired change in corneal depth (the nominal ablation profile) and dividing this by the attenuation function. This yields a new profile that, when ablated, results in the desired change.

In a particular embodiment the attenuation is achieved by computing the Zernike description of the ablation profile and dividing the Zernike polynomial by the attenuation profile that is entered into the laser beam delivery system:

$$P_{input}(\rho,\theta) = P_{desired}(\rho,\theta)/(A+B\rho+C\rho^2+D\rho^3+ \ldots +X\rho^n)$$

In a graph of a simple form of this function, $1-0.3r^2$, where $r_{max}=3.25$ mm (FIG. 4A), the radially dependent ablation efficiency varies from a value of approximately 1 proximate a central location wherein r≅0 on the corneal surface to a value of approximately 0.7 at a distance from the central location wherein r≅3.25 mm.

Figure 4A:
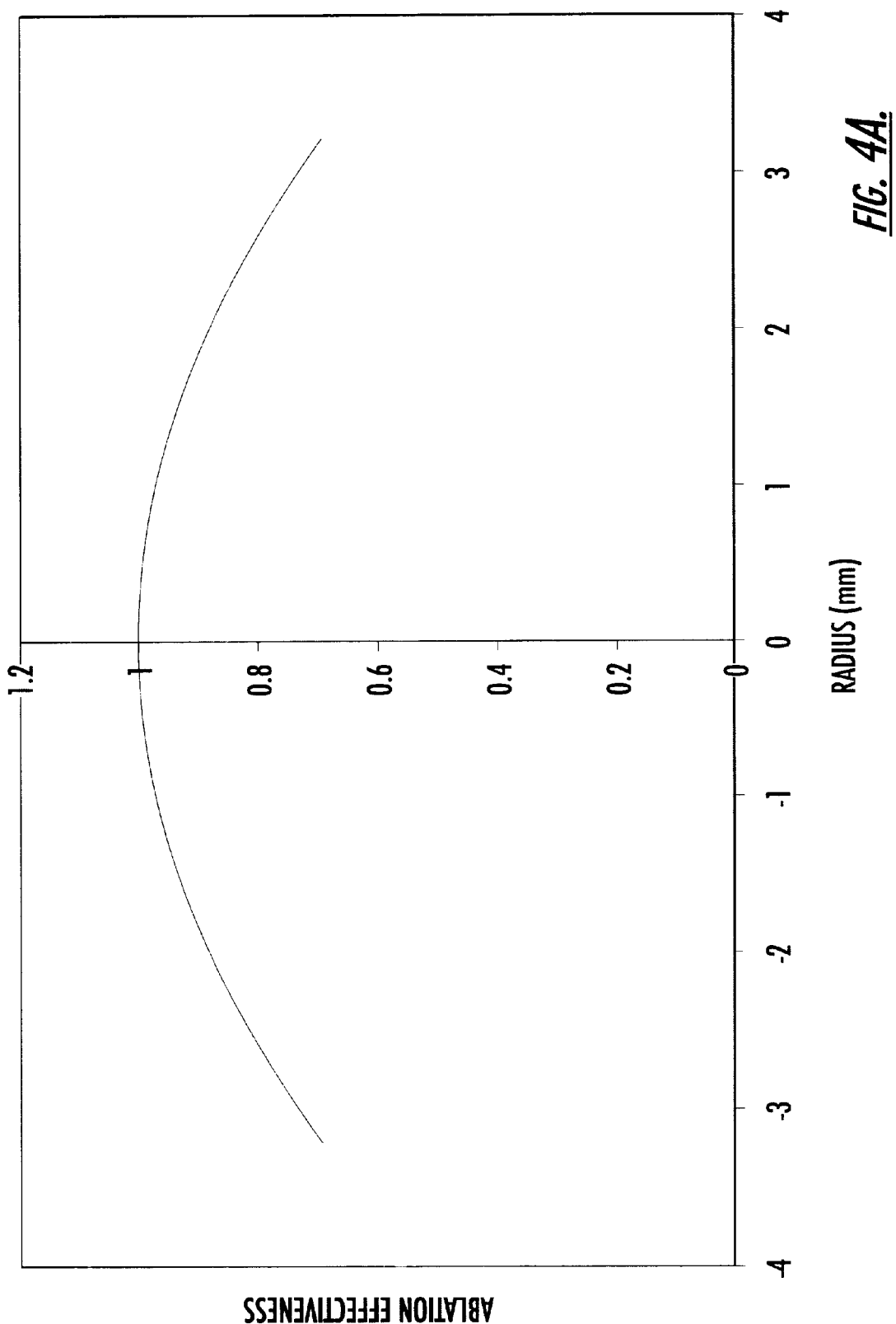
FIGS. 4A and 4B are graphs of the ablation efficiency function of the present invention.
Figure 4B:
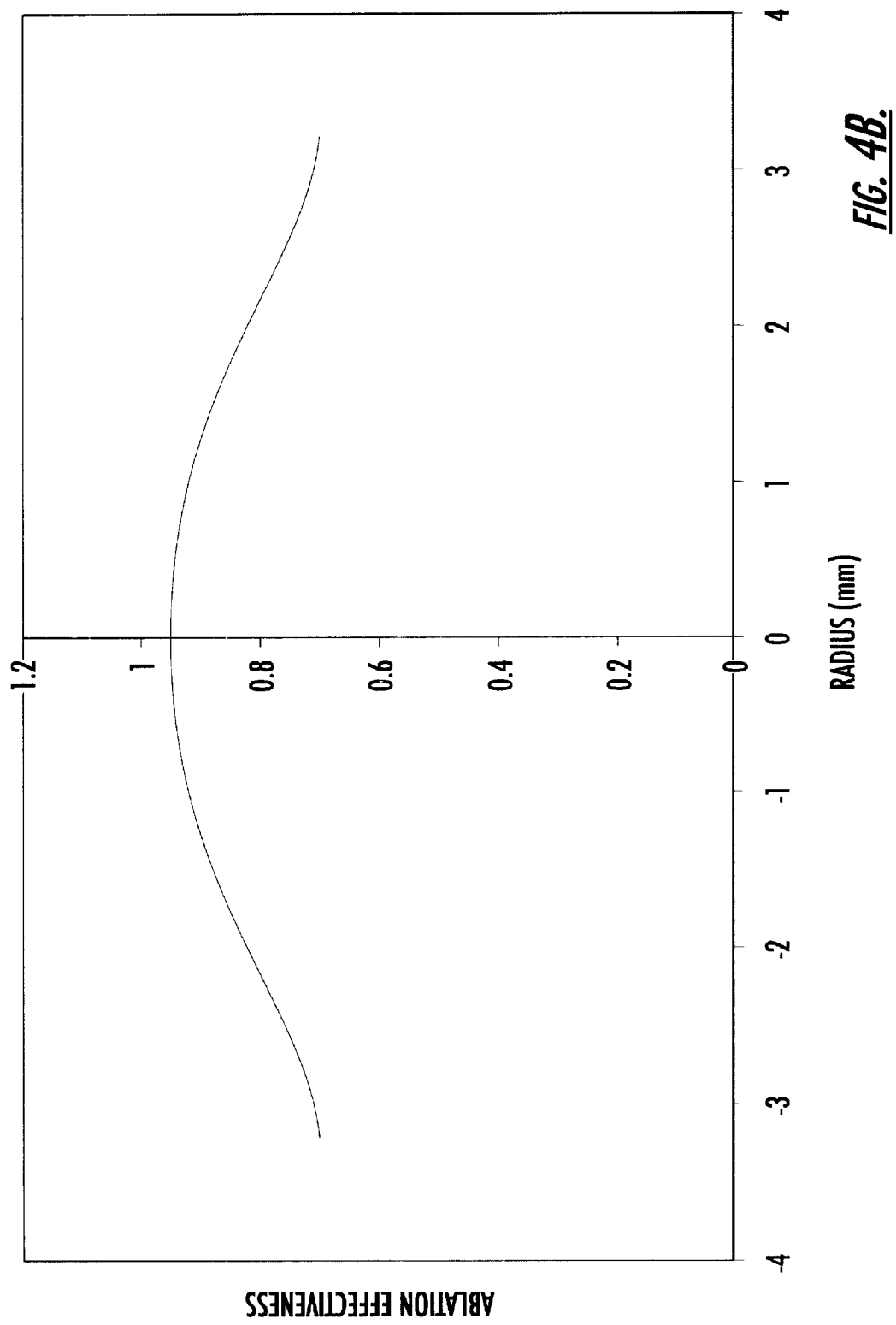
Figure 5:
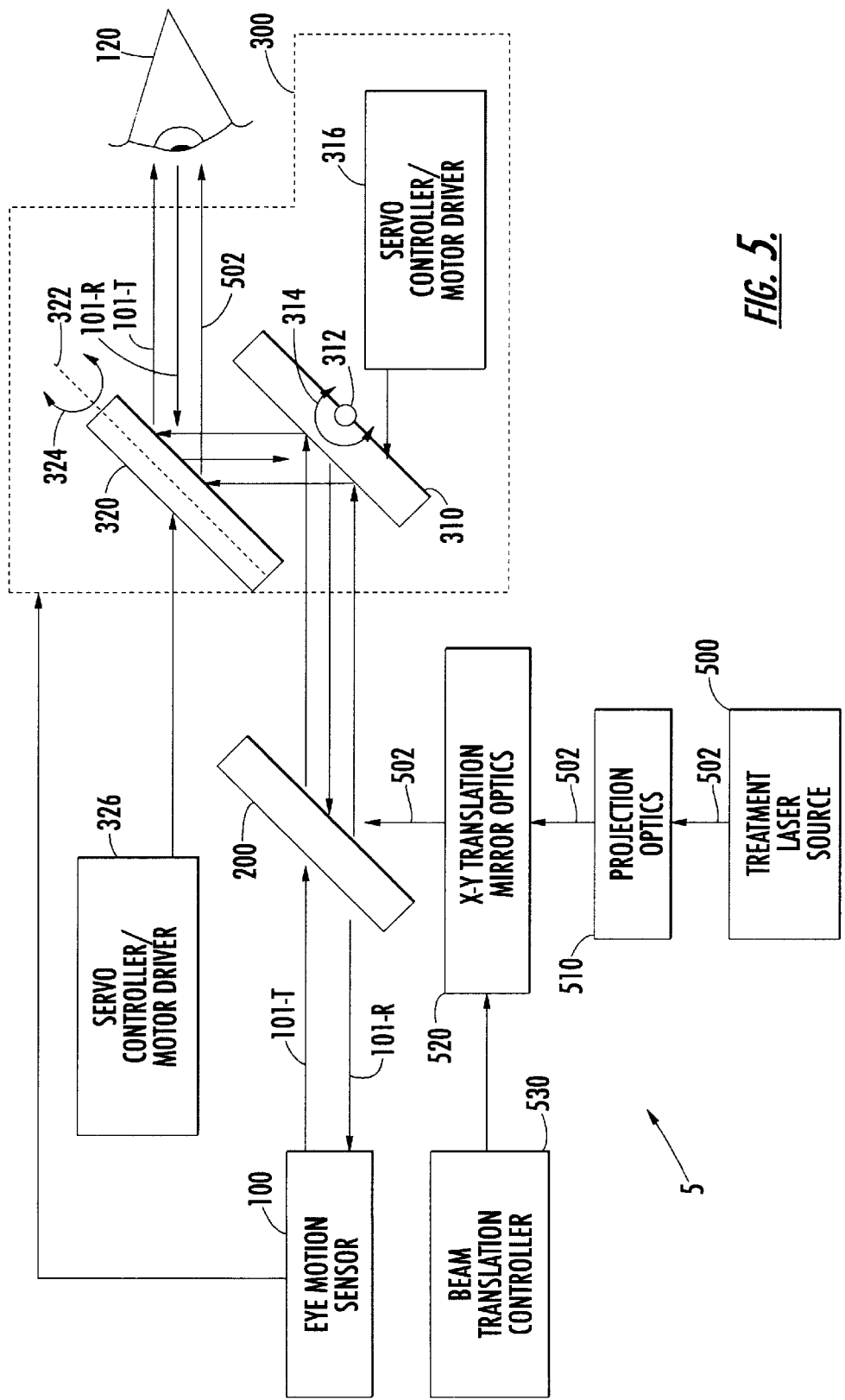
FIG. 5 is a schematic diagram of a system for delivering an ablative laser beam to an eye.

A more detailed version of the attenuation function, $0.95-0.32r^2 0.25r^3+0.3r^4$, which has a more complex shape, is shown in FIG. 4B. The specific function applied for a particular treatment laser system may depend on specifics of that device, such as beam energy, etc. Therefore, the coefficients in the attenuation function polynomial can be adjusted to optimize results for particular treatment conditions.

Preferably the optical correction is further based on refractive indices of media through which the wavefront passes. In a particular embodiment, the converter provides the path difference using a Zernike reconstruction of the wavefront, and the path difference is divided by a difference between an index of refraction of corneal material and an index of refraction of air. The optical correction is a prescribed alteration of corneal surface curvature of the eye, and the optical correction achieved by the reshaping of the corneal surface curvature of the eye is based on the prescribed alteration without regard to a resulting topography of the overall surface of the cornea.

An exemplary laser beam delivery system 5 (FIG. 5) laser beam delivery and eye tracking system may comprise, for example, that taught in U.S. Pat. No. 5,980,513, co-owned with the present application, the contents of which are incorporated herein by reference. The laser beam delivery portion of system 5 includes treatment laser source 500, projection optics 510, X-Y translation mirror optics 520, beam translation controller 530, dichroic beamsplitter 200, and beam angle adjustment mirror optics 300. The laser pulses are distributed as shots over the area to be ablated or eroded, preferably in a distributed sequence so that the desired shape of the object or cornea is achieved. Preferably the pulsed laser beam is shifted to direct the shots to a plurality of spatially displaced positions on the corneal surface to form a plurality of spatially distributed ablation spots. Each of these spots may have a predetermined diameter, for example, 2.5 or 1.0 mm, and may have an intensity distribution, for example, defined by a Gaussian or a generally flat distribution profile across the spot.

In operation of the beam delivery portion of system 5, laser source 500 produces laser beam 502 incident upon projection optics 510. Projection optics 510 adjusts the diameter and distance to focus of beam 502 depending on the requirements of the particular procedure being performed.

After exiting projection optics 510, beam 502 impinges on X-Y translation mirror optics 520, where beam 502 is translated or shifted independently along each of two orthogonal translation axes as governed by beam translation controller 530. Controller 530 is typically a processor programmed with a predetermined set of two-dimensional translations or shifts of beam 502 depending on the particular ophthalmic procedure being performed. Each of the X and Y axes of translation is independently controlled by a translating mirror.

The eye tracking portion of system 5 includes eye movement sensor 100, dichroic beamsplitter 200, and beam angle adjustment mirror optics 300. Sensor 100 determines the amount of eye movement and uses that amount to adjust mirrors 310 and 320 to track along with the eye movement. To do this, sensor 100 first transmits light energy 101-T, which has been selected to transmit through dichroic beamsplitter 200. At the same time, after undergoing beam translation in accordance with the particular treatment procedure, beam 502 impinges on dichroic beamsplitter 200, which has been selected to reflect beam 502 (e.g., a 193-nm wavelength laser beam) to beam angle adjustment mirror optics 300.

Light energy 101-T is aligned such that it is parallel to beam 502 as it impinges on beam angle adjustment mirror optics 300. It is to be understood that the term "parallel" as used herein includes the possibility that light energy 101-T and beam 502 can be coincident or collinear. Both light energy 101-T and beam 502 are adjusted in correspondence with one another by optics 300. Accordingly, light energy 101-T and beam 502 retain their parallel relationship when they are incident on eye 120. Since X-Y translation mirror optics 520 shifts the position of beam 502 in translation independently of optics 300, the parallel relationship between beam 502 and light energy 101-T is maintained throughout the particular ophthalmic procedure.

The beam angle adjustment mirror optics consists of independently rotating mirrors 310 and 320. Mirror 310 is rotatable about axis 312, as indicated by arrow 314, while mirror 320 is rotatable about axis 322, as indicated by arrow 324. Axes 312 and 322 are orthogonal to one another. In this way, mirror 310 is capable of sweeping light energy 101-T and beam 502 in a first plane (e.g., elevation), while mirror 320 is capable of independently sweeping light energy 101-T and beam 502 in a second plane (e.g., azimuth) that is perpendicular to the first plane. Upon exiting beam angle adjustment mirror optics 300, light energy 101-T and beam 502 impinge on eye 120.

The movement of mirrors 310 and 320 is typically accomplished with servo controller/motor drivers 316 and 326, respectively. In general, drivers 316 and 326 must be able to react quickly when the measured error from eye movement sensor 100 is large, and further must provide very high gain from low frequencies (DC) to about 100 radians per second to virtually eliminate both steady-state and transient error.

More specifically, eye movement sensor 100 provides a measure of the error between the center of the pupil (or an offset from the center of the pupil that the doctor selected) and the location where mirror 310 is pointed.

Light energy 101-R reflected from eye 120 travels back through optics 300 and beamsplitter 200 for detection at sensor 100. Sensor 100 determines the amount of eye movement based on the changes in reflection energy 101-R. Error control signals indicative of the amount of eye movement are fed back by sensor 100 to beam angle adjustment mirror optics 300. The error control signals govern the movement or realignment of mirrors 310 and 320 in an effort to drive the error control signals to zero. In doing this, light energy 101-T and beam 502 are moved in correspondence with eye movement while the actual position of beam 502 relative to the center of the pupil is controlled by X-Y translation mirror optics 520.

In order to take advantage of the properties of beamsplitter 200, light energy 101-T must be of a different wavelength than that of treatment laser beam 502. The light energy should preferably lie outside the visible spectrum so as not to interfere or obstruct a surgeon's view of eye 120. Further, if the present invention is to be used in ophthalmic surgical procedures, light energy 101-T must be "eye safe," as defined by the American National Standards Institute (ANSI). While a variety of light wavelengths satisfy the above requirements, by way of example, light energy 101-T may comprise infrared light energy in the 900-nm wavelength region. Light in this region meets the above-noted criteria and is further produced by readily available, economically affordable light sources. One such light source is a high pulse repetition rate GaAs 905-nm laser operating at 4 kHz, which produces an ANSI-defined eye-safe pulse of 10 nJ in a 50-ns pulse. A corneal ablation system using 193-nm ablation in a range of fluences of 100–1000 mJ/cm$^2$, which uses a small spot (<2.5 mm) may also be used. One preferred embodiment utilizes a spot <1.0 mm and 400–600 mJ/cm$^2$ peak fluences.

Thus it can be seen that the present invention provides a system and method for providing a compensating correction function adapted to negate or cancel out the ablation efficiency function to permit the actual desired shape of the corneal removal volume to be obtained, effecting an ideal optical result.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

That which is claimed is:

1. An optical correction system for correcting visual defects of an eye, the optical correction system comprising:
    a wavefront analyzer responsive to a wavefront emanating from an eye for determining an optical path difference between a reference wave and the wavefront;
    a converter for providing an optical correction based on the path difference and on a radially dependent ablation efficiency using a compensating polynomial of the form $A+B\rho+C\rho^2+D\rho^3+ \ldots +X\rho^n$, where $\rho$ is a normalized radius measured from a central portion of the cornea, reaching a value of 1 at an outer edge of the optical correction zone; and
    a laser beam having power sufficient for ablating corneal material, wherein the optical correction is achieved by the removal of a selected amount of the corneal material to create a desired corneal shape change.

2. The system recited in claim 1, further comprising:
    an energy source for generating a beam of optical radiation; and
    focusing optics disposed in the path of the beam for directing the beam through the eye, wherein the beam is reflected back from the retina of the eye as the wavefront of radiation emanating from the eye.

3. The system recited in claim 1, wherein the polynomial has the form $A+B\rho+C\rho^2+D\rho^3+E\rho^4$, with coefficients $A\cong0.95$, $B\cong0$, $C\cong-0.3$, $D\cong-0.25$, and $E\cong0.3$ for an optical zone radius of approximately 3.25 mm.

4. The system recited in claim 1, wherein the radially dependent ablation efficiency varies from a value of approximately 1.0 proximate a central location wherein $r\cong0$ on the corneal surface to a value of approximately 0.7 at an outer edge of the optical zone having a radius wherein $r\cong3.25$ mm.

5. The system recited in claim 1, wherein the optical correction is further based on refractive indices of media through which the wavefront passes.

6. The system recited in claim 1, further comprising an eye tracker for monitoring motion of the eye and for adjusting the positions of the laser beam responsive to the motion.

7. The system recited in claim 1, wherein the optical correction is a prescribed alteration of corneal surface curvature of the eye, and wherein the optical correction achieved by the reshaping of the corneal surface curvature of the eye is based on the prescribed alteration without regard to a resulting topography of the overall surface of the cornea.

8. The system recited in claim 1, wherein the converter provides the path difference using a Zernike reconstruction of the wavefront, and wherein the path difference is divided by a difference between an index of refraction of corneal material and an index of refraction of air.

9. A system for modifying vision of an eye, the system comprising:
    a wavefront analyzer responsive to a wavefront emanating from the eye for determining an optical path difference between a reference wave and the wavefront;
    a converter for providing an optical correction based on the optical path difference and a ablation efficiency using a compensating polynomial of the form: $A+B\rho+C\rho^2+D\rho^3+ \ldots +X\rho^n$, where $\rho$ is a normalized radius measured from a central portion of the cornea, reaching a value of 1 at an outer edge of the optical correction zone;
    a treatment laser producing a pulsed laser beam for providing a plurality of laser beam shots capable of ablating corneal material; and
    beam-shifting means operable with the treatment laser for shifting the pulsed laser beam and for directing the plurality of laser beam shots to a plurality of spatially displaced positions on the corneal surface of the eye as a plurality of spatially distributed ablation spots for providing a desired modification to the cornea thus modifying vision of the eye.

10. The system recited in claim 9, wherein the beam-shifting means provides a single predetermined shot pattern responsive to the optical correction.

11. The system recited in claim 9, wherein each of the plurality of ablation spots formed on the surface of the cornea may be defined by a diameter length of approximately 2.5 mm.

12. The system recited in claim 9, wherein each of the plurality of ablation spots formed on the surface of the cornea has a diameter of approximately 1.0 mm.

13. The system recited in claim 9, wherein each of the plurality of ablation spots formed on the surface of the cornea comprises an intensity profile across the spot defined by an approximately Gaussian distribution.

14. The system recited in claim 9, wherein each of the plurality of ablation spots formed on the surface of the cornea comprises a generally flat intensity profile across the spot.

15. The system recited in claim 9, wherein the optical correction is further based on refractive indices of media through which the wavefront passes.

16. The system recited in claim 9, wherein the polynomial has the form $A+B\rho+C\rho^2+D\rho^3+E\rho^4$, with coefficients $A\cong0.95$, $B\cong0$, $C\cong-0.3$, $D\cong-0.25$, and $E\cong-0.3$ for an optical zone radius of approximately 3.25 mm.

17. The system recited in claim 9, wherein the radially dependent ablation efficiency varies from a value of approximately 1.0 proximate a central location wherein r≅0 on the corneal surface to a value of approximately 0.7 at an outer edge of an optical zone having a radius of approximately 3.25 mm.

18. The system recited in claim 9, further comprising:

an energy source for generating a beam of optical radiation; and focusing optics disposed in the path of the beam for directing the beam through the eye, wherein the beam is reflected back from the retina of the eye as the wavefront of radiation emanating from the eye.

19. The system recited in claim 9, further comprising an eye tracker for monitoring motion of the eye and for adjusting the positions of the laser beam responsive to the motion.

20. The system recited in claim 9, wherein the optical correction comprises a prescribed alteration of corneal surface curvature of the eye, and wherein the optical correction achieved by the reshaping of the corneal surface curvature of the eye is based on the prescribed alteration without regard to a resulting topography of the overall surface of the cornea.

21. The system recited in claim 9, wherein the converter provides the path difference using a Zernike reconstruction of the wavefront, and wherein the path difference is divided by a difference between an index of refraction of corneal material and an index of refraction of air.

22. An optical correction prescriptive system for determining a correction for visual defects of an eye, the system comprising a converter for providing an optical correction based on an optical path difference between a reference wave and a wavefront emanating from an eye and on a radially dependent ablation efficiency using a compensating polynomial of the form $A+B\rho+C\rho^2+D\rho^3+\ldots+X\rho^n$, where $\rho$ is a normalized radius measured from a central portion of the cornea, reaching a value of 1 at an outer edge of the optical correction zone, the optical correction useful for determining an optimal amount of corneal material to be removed to create a desired corneal shape change.

23. A method of treating a cornea of an eye to effect a refractive correction of the eye, the method comprising the steps of:

determining a corneal modification from a measurement of the eye for providing a desired vision;

providing an optical correction for the eye based on the corneal modification and on a ablation efficiency using a compensating radially invariant polynomial of the form $A+B\rho+C\rho^2+D\rho^3+\ldots+X\rho^n$, where $\rho$ is a normalized radius measured from a central portion of the cornea, reaching a value of 1 at an outer edge of the optical correction zone;

directing a laser beam onto the eye for ablating the cornea; and moving the laser beam in a pattern about the eye, the pattern based on the optical correction.

24. The method recited in claim 23, further comprising the step of redirecting the laser beam to compensate for eye movement.

25. The method recited in claim 23, wherein the polynomial has the form $A+B\rho+C\rho^2+D\rho^3+E\rho^4$, with coefficients A≅0.95, B≅0, C≅−0.3, D≅−0.25, and E≅0.3 for an optical zone radius of approximately 3.25 mm.

26. The method recited in claim 23, further comprising the step of providing the optical correction based on refractive indices of media through which the wavefront passes.

27. The method recited in claim 23, wherein the radially dependent ablation efficiency varies from a value of approximately 1.0 proximate a central location wherein r≅0 on the corneal surface to a value of approximately 0.7 at an outer edge of an optical zone having a radius of approximately 3.25.

28. The method recited in claim 23, wherein the optical correction is a prescribed alteration of corneal surface curvature of the eye, and wherein the optical correction achieved by the reshaping of the corneal surface curvature of the eye is based on the prescribed alteration without regard to a resulting topography of the overall surface of the cornea.

29. The method recited in claim 23, further comprising the steps of:

selecting an area on the cornea; and providing a plurality of laser beam spots on the selected area of cornea for ablation thereof, wherein a size of each of the spots is substantially smaller that the selected area, and wherein the spots are in a pattern having a spacing therebetween.

30. The method recited in claim 29, further comprising the step of forming each of the plurality of ablation spots on the surface of the cornea to be defined by a diameter of approximately 2.5 mm.

31. The method recited in claim 29, further comprising the step of forming each of the plurality of ablation spots on the surface of the cornea to be defined by a diameter of approximately 1.0 mm.

32. The method recited in claim 29, further comprising the step of forming each of the plurality of ablation spots on the surface of the cornea to have an intensity distribution defined by a Gaussian profile across the spot.

33. The method recited in claim 29, further comprising the step of forming each of the plurality of ablation spots on the surface of the cornea to have an intensity distribution defined by a generally flat profile across the spot.

\* \* \* \* \*

UNITED STATES PATENT AND TRADEMARK OFFICE
CERTIFICATE OF CORRECTION

PATENT NO. : 6,569,154 B2  Page 1 of 1
DATED : May 27, 2003
INVENTOR(S) : John Alfred Campin et al.

It is certified that error appears in the above-identified patent and that said Letters Patent is hereby corrected as shown below:

Column 5,
Line 12, delete "$0.95-0.3r^2 0.25r^3+0.3r^4$" insert -- $0.95-0.3r^2-0.25r^3+0.3r_4$ --.

Signed and Sealed this

Fourth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,569,154 B2
DATED          : May 27, 2003
INVENTOR(S)    : John Alfred Campin et al.

It is certified that error appears in the above-identified patent and that said Letters Patent is hereby corrected as shown below:

Column 5,
Line 12, delete "$0.95-0.3r^2 0.25r^3+0.3r^4$" insert -- $0.95-0.3r^2-0.25r^3+0.3r^4$ --.

This certificate supersedes Certificate of Correction issued November 4, 2003.

Signed and Sealed this

Twenty-seventh Day of January, 2004

JON W. DUDAS
*Acting Director of the United States Patent and Trademark Office*